United States Patent
Govari et al.

(10) Patent No.: US 12,042,215 B2
(45) Date of Patent: Jul. 23, 2024

(54) MYOCARDIAL TISSUE ABLATION WITH NARROW TEMPERATURE VARIATION

(71) Applicant: BIOSENSE WEBSTER (ISRAEL) LTD., Yokneam (IL)

(72) Inventors: Assaf Govari, Haifa (IL); Andres Claudio Altmann, Haifa (IL); Ella Ozeri, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 547 days.

(21) Appl. No.: 16/522,938

(22) Filed: Jul. 26, 2019

(65) Prior Publication Data
US 2021/0022802 A1    Jan. 28, 2021

(51) Int. Cl.
*A61B 18/18* (2006.01)
*A61B 18/12* (2006.01)
(Continued)

(52) U.S. Cl.
CPC .......... *A61B 18/1492* (2013.01); *A61B 2017/00243* (2013.01); *A61B 2018/00351* (2013.01);
(Continued)

(58) Field of Classification Search
CPC ...... A61B 18/1492; A61B 2018/00351; A61B 2018/00577; A61B 2018/00642; A61B 18/1206; A61B 2017/00243; A61B 2018/00357; A61B 2018/00613; A61B 2018/00702; A61B 2018/00714;
(Continued)

(56) References Cited

U.S. PATENT DOCUMENTS

| 5,735,846 A | 4/1998 | Panescu |
| 5,743,903 A | 4/1998 | Stern |

(Continued)

FOREIGN PATENT DOCUMENTS

EP    3375396 A1    9/2018

OTHER PUBLICATIONS

Di Donna, Paolo, et al. "Efficacy of catheter ablation for atrial fibrillation in hypertrophic cardiomyopathy: impact of age, atrial remodeling, and disease progression." Europace 12.3 (2010).

(Continued)

*Primary Examiner* — Michael F Peffley
*Assistant Examiner* — Amanda L Zink

(57) ABSTRACT

A system including a medical probe having a tube with a distal end for insertion into a cardiac chamber, an electrode at the distal end that conveys energy to myocardial tissue, a temperature sensor at the distal end that outputs a signal indicating a temperature of the tissue, a channel contained within the tube that delivers fluid to the distal end, and a fluid port at the distal end and coupled to the channel. The system also includes a generator that applies a specified level of the energy to the electrode, a pump that forces the fluid into the channel at a controllable rate, and a processor that controls the rate responsively to the signal so that a difference between a specified temperature, which is no greater than 55° C., and the indicated temperature is no greater than ±2.5° C. while the generator applies a constant level of the energy.

18 Claims, 3 Drawing Sheets

(51) Int. Cl.
*A61B 18/14* (2006.01)
*A61B 17/00* (2006.01)
*A61B 18/00* (2006.01)

(52) U.S. Cl.
CPC .............. *A61B 2018/00577* (2013.01); *A61B 2018/00642* (2013.01); *A61B 2018/00702* (2013.01); *A61B 2018/00714* (2013.01); *A61B 2018/00797* (2013.01); *A61B 2018/00839* (2013.01); *A61B 2218/002* (2013.01)

(58) Field of Classification Search
CPC ........... A61B 2018/00744; A61B 2018/00791; A61B 2018/00797; A61B 2018/00821; A61B 2018/00839; A61B 2218/002; A61N 7/022
See application file for complete search history.

(56) References Cited

U.S. PATENT DOCUMENTS

| | | | |
|---|---|---|---|
| 5,868,743 A | 2/1999 | Saul | |
| 6,063,078 A | 5/2000 | Wittkampf | |
| 6,210,406 B1* | 4/2001 | Webster | A61B 18/1492 606/41 |
| 8,954,161 B2* | 2/2015 | McCarthy | A61B 5/6852 607/102 |
| 9,277,961 B2* | 3/2016 | Panescu | A61B 18/02 |
| 2003/0004506 A1* | 1/2003 | Messing | A61B 18/1492 606/41 |
| 2008/0004534 A1* | 1/2008 | Gelbart | A61B 5/029 600/508 |
| 2011/0270247 A1* | 11/2011 | Sherman | A61B 18/082 606/41 |
| 2012/0165812 A1 | 6/2012 | Christian | |
| 2017/0143401 A1* | 5/2017 | Woloszko | A61B 18/1206 |
| 2017/0312008 A1* | 11/2017 | Harlev | A61M 25/001 |
| 2020/0015880 A1* | 1/2020 | Curley | A61B 18/1477 |

OTHER PUBLICATIONS

Calkins, Hugh, et al. "Temperature monitoring during radiofrequency catheter ablation procedures using closed loop control. Atakr Multicenter Investigators Group." Circulation 90.3 (1994).
European Search Report for corresponding EPA No. 20187664.6 dated Dec. 4, 2020.

* cited by examiner

MYOCARDIAL TISSUE ABLATION WITH NARROW TEMPERATURE VARIATION

FIELD OF THE INVENTION

The present invention relates generally to cardiac ablation, and specifically to controlling the temperature of myocardial tissue during an ablation procedure.

BACKGROUND OF THE INVENTION

During an ablation procedure on a heart, there may be local overheating of the heart surface being ablated, as well as of the heart tissue underlying the surface. The surface overheating may be manifested as charring, and the overheating of the underlying tissue may cause other damage to the tissue, even leading to penetration of the tissue causing additional problems. To monitor and control the temperature of the surface and the underlying tissue, as well as to estimate the temperature of the tissue, a temperature sensor may be positioned within a distal tip of the catheter, and the region being ablated may be irrigated with an irrigation fluid, typically saline, in order to prevent charring.

The research paper by Di Donna, Paolo, et al. "Efficacy of catheter ablation for atrial fibrillation in hypertrophic cardiomyopathy: impact of age, atrial remodeling, and disease progression." Europace 12.3 (2010), assessed the outcome of a multicenter hypertrophic cardiomyopathy cohort following radiofrequency catheter ablation for symptomatic atrial fibrillation refractory to medical therapy. This research paper describes using an irrigation rate of 20-30 ml/min in order to maintain, in a tip of an open irrigated-tip catheter, a temperature below 45° C.

The research paper by Calkins, Hugh, et al. "Temperature monitoring during radiofrequency catheter ablation procedures using closed loop control. Atakr Multicenter Investigators Group." Circulation 90.3 (1994), evaluated electrode temperatures obtained using a radiofrequency ablation system that incorporates closed loop feedback control to achieve preset target electrode temperatures and to determine if closed loop temperature control results in a lower incidence of developing a coagulum. While automatically modulating the amount of power delivered (range, 0.5 W-50 W) so that the tip temperature approaches but does not exceed the selected target temperature (40°-95° C.) by more than 5° C., this research paper determined that successful ablation could be achieved with the electrode tip temperature being as low as 44° C.

U.S. Pat. No. 5,868,743 to Saul, et al., describes a method of targeting and ablating cardiac tissue. The method describes modulating the delivered ablation power between 0.5-5.0 W using feedback from a catheter-embedded thermocouple in order to attempt to achieve a selected target temperature of between 45° C.-95° C. The method also describes a mode of operation that achieves a tissue temperature below 52° C., and preferably in the range of 48° C.-52° C.

U.S. Pat. No. 5,735,846 to Panescu, et al., describes systems and methods for ablating body tissue using an electrode for contacting tissue at a tissue-electrode interface to transmit ablation energy at a determinable power level. The method includes applying 30 W of radiofrequency catheter ablation power in order to achieve ablation temperatures between 45° C.-50° C.

U.S. Pat. No. 5,743,903 to Stern, et al., describes a cardiac ablation system and method that uses an ablation electrode having an energy emitting body. The system can maintain the temperature of the tissue undergoing ablation can also above a prescribed minimum temperature condition (e.g. 40° C.)

U.S. Pat. No. 6,063,078 to Wittkampf describes methods and systems for ablating tissue within a body. The system includes a control that can be aimed so that a constant power to the electrode is maintained, or a constant temperature of the tip electrode is maintained.

SUMMARY OF THE INVENTION

There is provided, in accordance with an embodiment of the present invention, an irrigated ablation system including a medical probe including a flexible insertion tube having a distal end configured to be inserted into a chamber of a heart, an ablation electrode disposed at the distal end and configured to convey ablation energy to a region of myocardial tissue with which the electrode is in contact, a temperature sensor disposed at the distal end and configured to output a temperature signal indicative of a temperature of the region of myocardial tissue, a channel contained within the insertion tube and configured to deliver an irrigation fluid to the distal end, and one or more fluid ports coupled to the channel and disposed at the distal end. The irrigated ablation system also includes an ablation energy generator configured to apply a specified level of the ablation energy to the ablation electrode, a pump configured to force the irrigation fluid into the channel at a controllable pumping rate, and a processor configured to control the pumping rate responsively to the temperature signal so that a difference between a specified ablation temperature, which is no greater than 55° C., and the indicated temperature is no greater than ±2.5° C. while the ablation energy generator delivers a constant level of the ablation energy to the ablation electrode.

In some exemplary embodiments, the medical probe includes an intracardiac catheter.

In additional exemplary embodiments, the irrigation fluid includes a saline solution.

In further exemplary embodiments, the specified ablation temperature is at least 42° C.

In supplementary exemplary embodiments, the temperature sensor includes a thermocouple.

In one exemplary embodiment, the irrigated ablation system may also include a temperature module configured to receive the temperature signal from the temperature sensor, to compute, based on the temperature signal, a temperature value, and wherein the processor is configured to control the pumping rate responsively to the temperature signal by controlling the pumping rate responsively to the temperature value. In some exemplary embodiments, the processor is configured to control the pumping rate responsively to the temperature signal by applying a proportional-integral-derivative controller (PID) algorithm to the indicated temperature.

In additional exemplary embodiments, the ablation energy can be selected from a list consisting of radiofrequency (RF) energy, high-intensity focused ultrasound (HIFU) energy and pulsed field ablation (PFA) energy.

There is also provided, in embodiments of the present invention, a method including applying a specified level of ablation energy to an ablation electrode disposed at a distal end of a medical probe inserted into a chamber of a heart and in contact with a region of myocardial tissue, receiving, by a processor from a temperature sensor disposed at the distal end, a signal indicative of a temperature of the region of myocardial tissue, and controlling a pumping rate of irrigation fluid to one or more fluid ports disposed at the distal end distal end responsively to the temperature signal so that a difference between a specified ablation temperature, which is no greater than 55° C., and the indicated temperature is no greater than ±2.5° C. while delivering a constant level of the ablation energy to the ablation electrode.

There is also provided, in embodiments of the present invention, a computer software product, operated in conjunction with an intracardiac catheter having a distal end inserted into a chamber of a heart, a channel contained within the insertion tube and configured to deliver an irrigation fluid to the distal end, and one or more fluid ports coupled to the channel and disposed at the distal end, the product including a non-transitory computer-readable medium, in which program instructions are stored, which instructions, when read by a computer, cause the computer to apply a specified level of ablation energy to an ablation electrode disposed at the distal end and configured to convey ablation energy to a region of myocardial tissue with which the electrode is in contact to receive, from a temperature sensor disposed at the distal end, a temperature signal indicative of a temperature of the region of myocardial tissue, and to control a pumping rate of irrigation fluid to the one or more fluid ports end responsively to the temperature signal so that a difference between a specified ablation temperature, which is no greater than 55° C., and the indicated temperature is no greater than ±2.5° C. while delivering a constant level of the ablation energy to the ablation electrode.

BRIEF DESCRIPTION OF THE DRAWINGS

The disclosure is herein described, by way of example only, with reference to the accompanying drawings, wherein.

DETAILED DESCRIPTION OF EMBODIMENTS

Embodiments of the present invention describe systems and methods for maintaining the temperature of myocardial tissue within a specified range during an ablation procedure. As described hereinbelow, the system comprises a medical probe, an ablation energy generator, a pump, and a processor.

The medical probe comprises a flexible insertion tube having a distal end configured to be inserted into a chamber of a heart, and an electrode disposed at the distal end and configured to convey ablation energy to a region of myocardial tissue with which the electrode is in contact. The medical probe also comprises a temperature sensor disposed at the distal end and configured to output a temperature signal indicative of a temperature of the region of myocardial tissue. The medical probe further comprises a channel contained within the insertion tube and configured to deliver an irrigation fluid to the distal end. The medical probe additionally includes one or more fluid ports coupled to the channel and disposed at the distal end.

As described hereinbelow, the ablation energy generator is configured to apply a specified level of the ablation energy to the ablation electrode, and the pump is configured to force the irrigation fluid into the channel at a controllable pumping rate. In exemplary embodiments of the present invention, the processor is configured to control the pumping rate responsively to the temperature signal so that a difference between a specified ablation temperature, which is typically no greater than 55° C., and an indicated or target temperature, is no greater than ±2.5° C. while the ablation signal generator delivers a constant level of the ablation energy to the ablation electrode.

By keeping the temperature variation of the myocardial tissue to a narrow range (e.g., ±2.5° C.), and by keeping the mean temperature at a relatively low value (e.g., below about 55° C.), systems implementing exemplary embodiments of the invention can help reduce the risk of heat-based complications (e.g., steam-pops) during ablation procedures.

System Description

Figure 1:
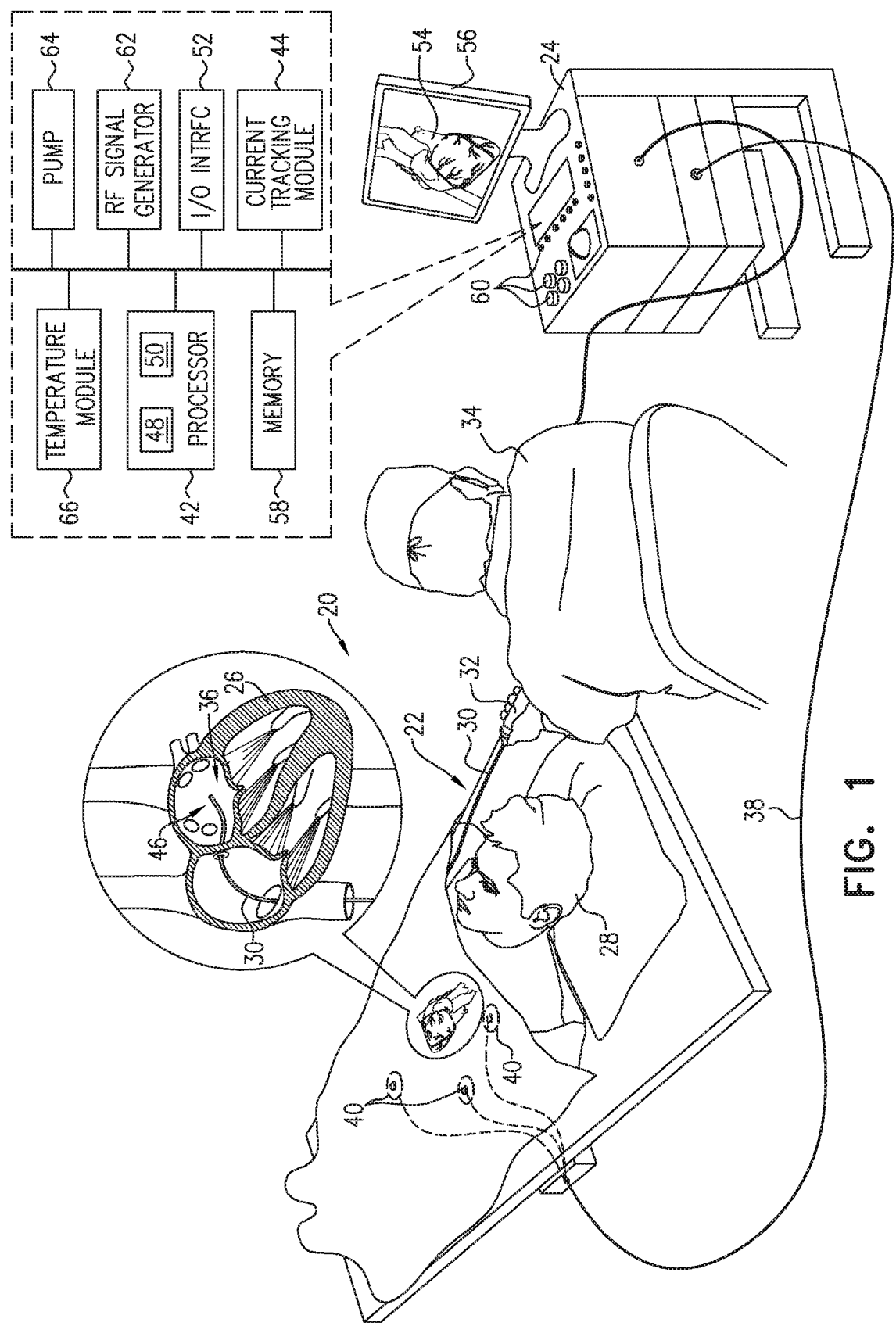
FIG. 1 is a schematic, pictorial illustration of a medical system comprising an ablation catheter, in accordance with an embodiment of the present invention.

FIG. 1 is a schematic, pictorial illustration of a medical system 20 comprising a medical probe 22 and a control console 24, in accordance with an embodiment of the present invention. Medical system 20 may be based, for example, on the CARTO® system, produced by Biosense Webster Inc. (Diamond Bar, California, U.S.A.). In embodiments described hereinbelow, medical probe 22 comprises an intracardiac catheter that can be used for diagnostic or therapeutic treatment, such as for ablating tissue in a heart 26 of a patient 28. Medical probe 22 may also be referred to as an ablation catheter.

Medical probe 22 comprises an insertion tube 30 and a handle coupled to a proximal end of the insertion tube. By manipulating handle 32, a medical professional 34 can insert a distal end 36 of medical probe 22 into a body cavity in patient 28. For example, medical professional 34 can insert medical probe 22 through the vascular system of patient 28 so that distal end 36 enters a chamber of heart 26 and engages myocardial tissue at a desired location or locations.

Control console 24 is connected, by a cable 38 to body surface electrodes, which typically comprise adhesive skin patches 40 that are affixed to patient 28. Control console 24 comprises a processor 42 that, in conjunction with a current tracking module 44, determines position coordinates of distal end 36 inside heart 26 based on impedances measured between adhesive skin patches 40 and a location electrode 46 that is disposed at distal end 36, as described in the description referencing FIG. 2 hereinbelow. Location electrode 46 is connected to control console 24 by wires (not shown) running through medical probe 22.

Processor 42 may comprise real-time noise reduction circuitry 48 typically configured as a field programmable gate array (FPGA), followed by an analog-to-digital (A/D) ECG (electrocardiograph) signal conversion integrated circuit 50. The processor can pass the signal from A/D ECG circuit 50 to another processor and/or can be programmed to perform one or more algorithms disclosed herein, each of the one or more algorithms comprising steps described hereinbelow. The processor uses noise reduction circuitry 48 and A/D ECG circuit 50 as well as features of modules which are described in more detail below, in order to perform the one or more algorithms presented in exemplary embodiments described herein.

The medical system shown in FIG. 1 uses impedance-based sensing to measure a location of distal end 36; however, other position tracking techniques may be used (e.g., techniques using magnetic-based sensors). Impedance-based position tracking techniques are described, for example, in U.S. Pat. Nos. 5,983,126, 6,456,864 and 5,944,022. The methods of position sensing described hereinabove are implemented in the above-mentioned CARTO® system and are described in detail in the patents cited above.

Control console 24 also comprises an input/output (I/O) communications interface 52 that enables the control console to transfer signals from, and/or transfer signals to electrode 46 and adhesive skin patches 40. Based on signals received from electrode 46 and/or adhesive skin patches 40, processor 42 can generate can generate a map 54 that shows the position of distal end 36 in the patient's body.

During a procedure, processor 42 can present map 54 to medical professional 34 on a display 56, and store data representing the electroanatomical LAT map in a memory 58. Memory 58 may comprise any suitable volatile and/or non-volatile memory, such as random access memory or a hard disk drive.

In some exemplary embodiments, medical professional 34 can manipulate map 54 using one or more input devices 60. In alternative exemplary embodiments, display 56 may comprise a touchscreen that can be configured to accept inputs from medical professional 34, in addition to presenting map 54.

Control console 24 also comprises an ablation energy generator such as a radio-frequency (RF) signal generator 62. While exemplary embodiments herein describe using RF energy from RF signal generator 62 to ablate tissue in heart 26, using other types of ablation energy is considered to be within the spirit and scope of the present invention. For example, the ablation energy generator may be configured to generate other types of ablation energy such as high-intensity focused ultrasound (HIFU) energy and pulsed field ablation (PFA) energy. Pulsed field ablation can also be referred to as irreversible electroporation (IRE).

In the configuration shown in FIG. 1, control console 24 additionally comprises a pump 64 and a temperature module 66. The respective functionalities of RF signal generator 62, pump 64 and temperature module 66 are described in the description referencing FIG. 2 hereinbelow.

Figure 2:
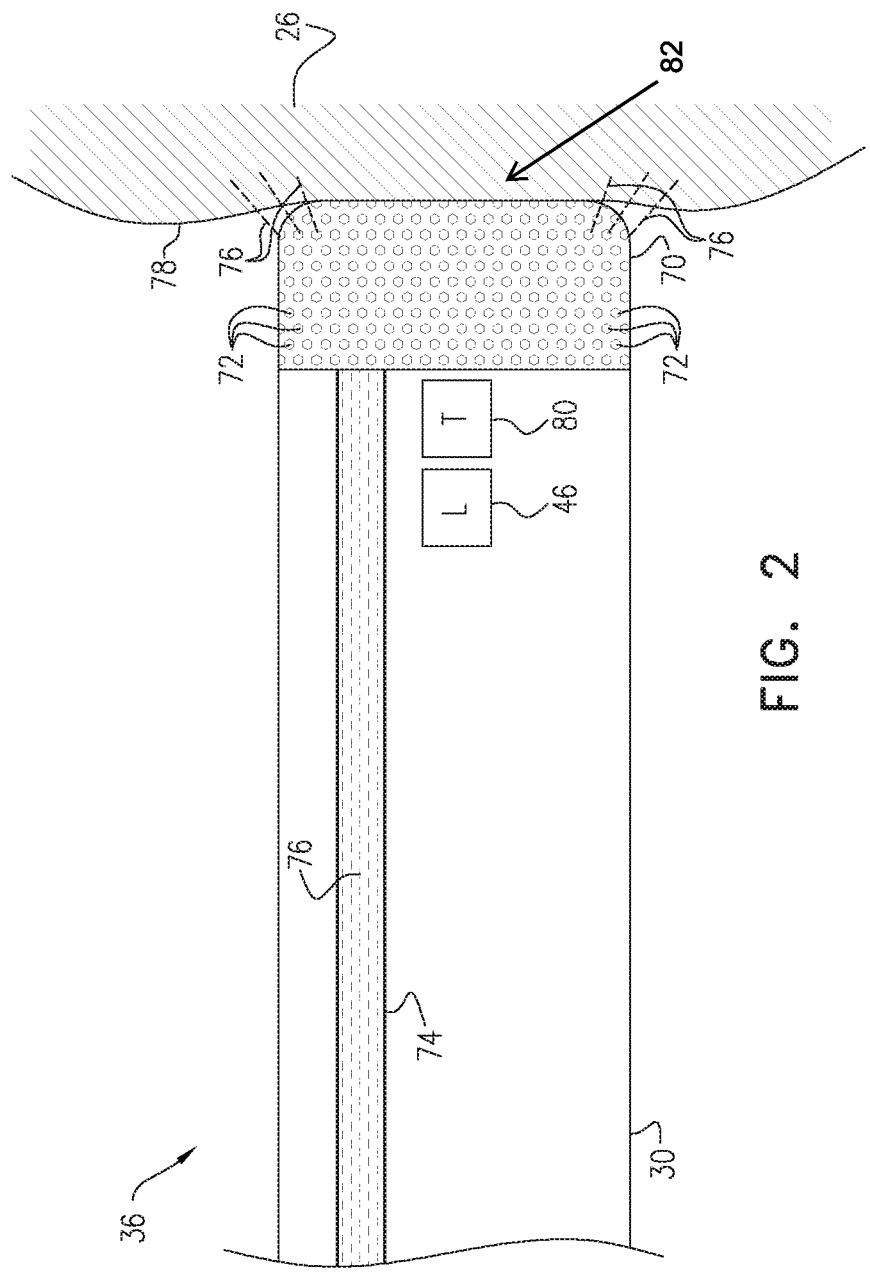
FIG. 2 is a schematic cross-sectional longitudinal view of a distal end of the ablation catheter, in accordance with an embodiment of the present invention.

FIG. 2 is a schematic cross-sectional longitudinal view of distal end 36, in accordance with an exemplary embodiment of the present invention. In the configuration shown in FIG. 2, medical probe 22 comprises location electrode 46 and an ablation electrode 70 disposed at distal end 36. Ablation electrode 36 typically comprises a thin metal layer formed over distal end 36. Ablation electrode 70 is connected to RF signal generator 62 by conductors (not shown) in insertion tube 30.

In the configuration shown in FIG. 1, RF signal generator 62 is configured to apply RF energy to ablation electrode 70. In operation, ablation electrode 70 conveys applied RF energy to a region 82 of myocardial tissue 78 that is in contact with the ablation electrode 70, thereby ablating the myocardial tissue 78. In exemplary embodiments of the present invention, RF signal generator 62 can, in response to instructions (i.e., power signals) from processor 42, monitor and control ablation parameters such as the level, the frequency and the duration of RF energy applied to ablation electrode 70.

Ablation electrode 70 comprises a plurality of fluid ports 72. In the configuration shown in FIG. 2, fluid ports 72 are disposed at distal end 36 within ablation electrode 70. Medical probe 22 also comprises a channel 74 (e.g., tubing) that is contained within insertion tube 30. A first end of channel 74 is coupled to fluid ports 72, and a second end of the channel is coupled to pump 64.

Pump 64 forces irrigation fluid 76 (e.g., a saline solution) into channel 74, and fluid ports 72 convey the pumped irrigation fluid to myocardial tissue 78 in order to irrigate and thereby control the temperature of the myocardial tissue during an ablation procedure. In exemplary embodiments of the present invention, pump 64 can, in response to instructions received from processor 42, control a rate of flow of irrigation fluid 76 from the pump 64.

Medical probe 22 further comprises a temperature sensor 80 (e.g., a thermocouple) disposed at distal end 36 of probe 22. Temperature sensor 80 generates a temperature signal indicating a temperature of myocardial tissue 78 in contact with ablation electrode 70. Temperature sensor 80 is connected to temperature module 66 by conductors (not shown) in insertion tube 30. In operation, temperature module 66 analyzes the temperature signal received from temperature sensor 80 located at the distal end 36 of the probe 22 so as to determine the temperature indicated by the temperature signal.

While the configuration of medical probe 22 in FIG. 2 shows distal end 36 comprising a single ablation electrode 70 and a single temperature sensor 80, configurations of the medical probe with the distal end comprising multiple ablation electrodes 70 and/or multiple temperature sensors 80 are considered to be within the spirit and scope of the present invention.

Myocardial Tissue Temperature Control

Figure 3:
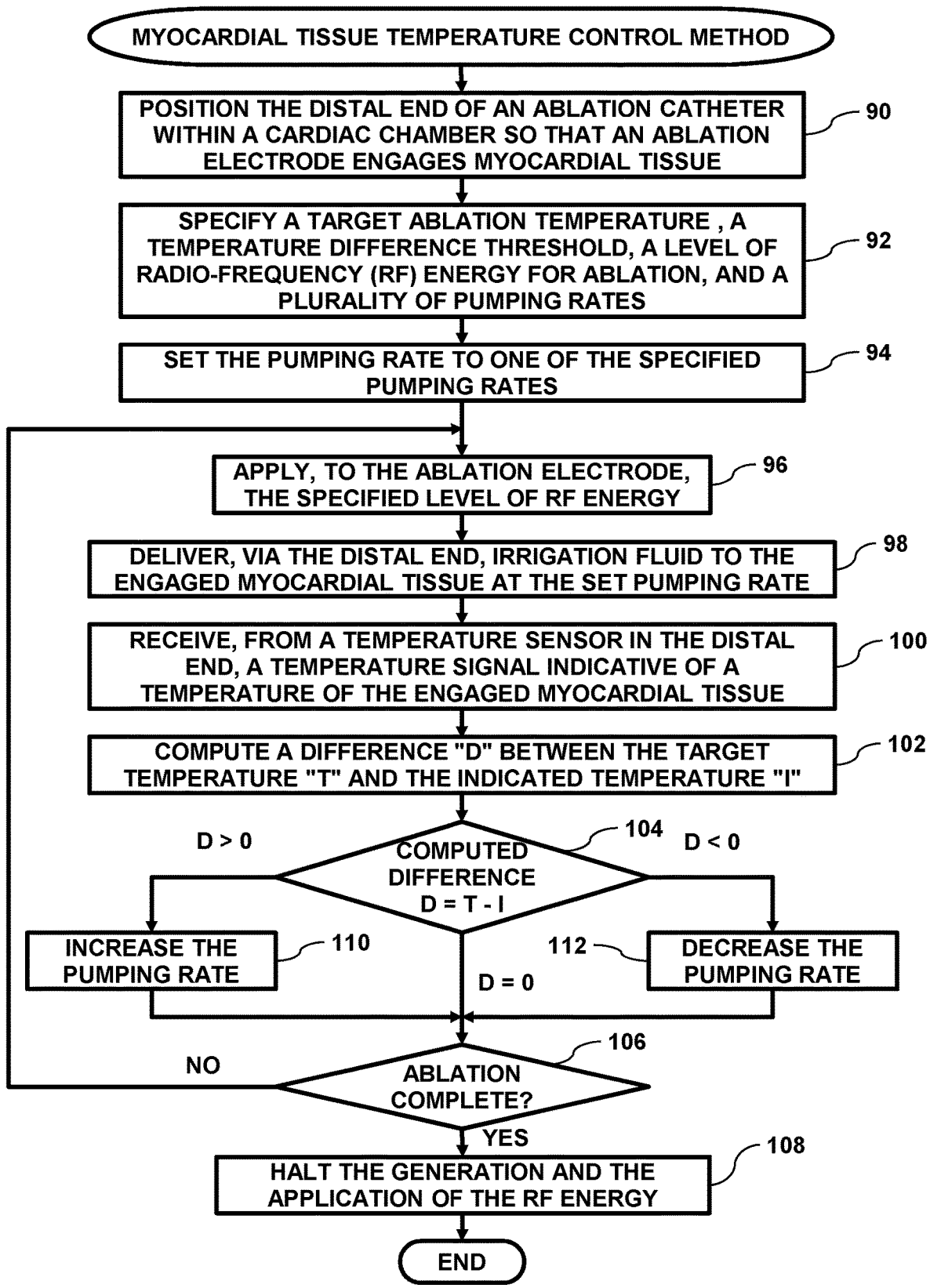
FIG. 3 is a flow diagram that schematically illustrates a method of controlling the temperature of myocardial tissue during an ablation procedure, in accordance with an embodiment of the present invention.

FIG. 3 is a flow diagram that schematically illustrates a method for maintaining the temperature of region 82 of myocardial tissue 78 within a specified range during an ablation procedure, in accordance with an exemplary embodiment of the present invention. In a positioning step 90, medical professional 34 inserts distal end 36 into a chamber of heart 26 and manipulates handle 32 so that ablation electrode 70 engages a targeted region 82 of myocardial tissue 78.

In a specification step 92, processor 42 specifies ablation procedure parameters comprising a target ablation temperature, a temperature difference threshold, a level or radio-frequency (RF) energy for ablation and a plurality of pumping rates for irrigation fluid 76. In one exemplary embodiment, processor 42 can retrieve one or more of the ablation procedure parameters from memory 58. In another exemplary embodiment, processor 42 can receive inputs from medical professional 34 (e.g., via input devices 60) specifying one or more of the ablation procedure parameters.

The following are examples for the ablation procedure parameters:

In one exemplary embodiment, the target ablation temperature can be below a maximum temperature such as 55° C. In another embodiment, the target ablation temperature can be within a defined temperature range such as 42° C.-55° C.

In some exemplary embodiments, the temperature difference threshold may comprise ±2.5° C. (i.e., in relation to the target ablation temperature).

In some exemplary embodiments, the specified level of RF energy can be a power level within a defined range (e.g., 20 W-90 W).

In some exemplary embodiments, the plurality of pumping rates may comprise a low pumping rate of 2 ml/minute, an intermediate pumping rate of 10 ml/minute and a high pumping rate of 25 ml/minute. In an alternative embodiment, the pumping rates may be continuously variable between the low pumping rate and the high pumping rate.

In an initialization step 94, processor 42 sets the pumping rate for pump 64 to one of the specified pumping rates. For example, processor 42 can convey a pump signal to pump 64 instructing the pump to initially set the pumping rate to the intermediate pumping rate of 10 ml/minute.

In an application step 96, processor 42 conveys a power signal to RF signal generator 62 instructing the RF signal generator to generate a specific level of RF energy and to apply (i.e. convey) the generated RF energy to ablation electrode 70.

In a delivery step 98, pump 64 forces irrigation fluid 76 into channel 74 at the set pumping rate, and the irrigation fluid exits distal end 36 via fluid ports 72, thereby irrigating the region of myocardial tissue 78.

In a receive step 100, processor 42 receives, from temperature sensor 80, a temperature signal indicative of a temperature of the engaged region of myocardial tissue 78. In some exemplary embodiments, temperature module 66 can receive the temperature signal from temperature sensor 80, compute, based on the temperature signal, a temperature value, and convey, to processor 42, the computed temperature value (also referred to herein as the indicated temperature).

In a computation step 102, processor 42 computes a difference "D" between the target ablation temperature "T" and the indicated temperature "I" using the formula $$D=T-I.$$

In a first comparison step 104, if D=0, then in a first adjustment step 106, processor 42 conveys a pump signal to pump instructing the pump to set the pumping rate to the intermediate pumping rate. In some exemplary embodiments, processor 42 may allow for noise so that the condition D=0 is true if D=0±0.2° C.

In a second comparison step 106, if the ablation procedure is not complete, then the method continues with step 96. If the ablation procedure is complete, then in a halt step 108, processor 42 conveys a power signal instructing RF signal generator 62 to halt generation and application of the specified level of RF energy, and the method ends.

Returning to step 104, if D>0, then in a second adjustment step 110, processor 42 conveys a pump signal to pump 64 instructing the pump to increase the pumping rate. In one embodiment, processor 42 can increase the pumping rate by conveying a pump signal to pump 64 that instructs the pump to set the pumping rate to the high pumping rate. In another embodiment, processor 42 can increase the pumping rate by conveying a pump signal to pump 64 that instructs the pump to increase the pumping rate by a specified value (e.g., increase by 2 ml/minute).

In an additional exemplary embodiment, processor 42 can apply an algorithm such as a proportional-integral-derivative controller (PID) algorithm to analyze the indicated temperature in order to control a continuously variable flow of irrigation fluid 76. In this additional exemplary embodiment, if pump 64 forces irrigation fluid 76 into channel 74 at the high pumping rate while the indicated temperature exceeds a specified maximum temperature (e.g., 55° C.) for longer than a specified time period (e.g., 5 seconds), processor 42 can use a variation of the PID algorithm that is configured to instruct RF signal generator 62 to reduce the level of RF energy applied to ablation electrode 70.

Returning to step 104, if D<0, then in a third adjustment step 112, processor 42 conveys a pump signal to pump 64 instructing the pump to decrease the pumping rate. In one exemplary embodiment, processor 42 can decrease the pumping rate by conveying a pump signal to pump 64 that instructs the pump to set the pumping rate to the low pumping rate. In another exemplary embodiment, processor 42 can decrease the pumping rate by conveying a pump signal to pump 64 that instructs the pump to decrease the pumping rate by a specified value (e.g., decrease by 2 ml/minute). In embodiments of the present invention, processor 42 conveys, in response to the indicated temperature, pump signals instructing pump 64 to adjust the pumping rate while RF signal generator generates a constant specific level of RF energy. In other words, while continuously generating the specific level of RF energy, medical console 24 adjusts the pumping rate for irrigation fluid 76 in order to maintain the temperature of the myocardial tissue being treated at or near the target ablation temperature.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An irrigated ablation system, comprising:
a medical probe comprising:
a flexible insertion tube having a distal end configured to be inserted into a chamber of a heart;
an ablation electrode comprising one or more fluid ports extending therethrough, wherein the ablation electrode is disposed at the distal end and configured to convey ablation energy to a region of myocardial tissue with which the electrode is in contact and wherein at least one of the one or more fluid ports extends through the most distal surface of the ablation electrode configured to abut the myocardial tissue during ablation;
a temperature sensor disposed at the distal end and configured to output a temperature signal indicative of a temperature of the region of myocardial tissue concurrently with conveying the ablation energy to the region of the myocardial tissue;
a channel contained within the insertion tube and configured to deliver an irrigation fluid to the distal end through the one or more fluid ports of the ablation electrode; and
an ablation energy generator configured to apply a specified level of the ablation energy to the ablation electrode;
a pump configured to force the irrigation fluid into the channel at a controllable pumping rate; and
a processor configured to dynamically control the pumping rate concurrently with conveying the ablation energy to the region of the myocardial tissue, responsively to the temperature signal so that a difference between a specified ablation temperature, which is no greater than 55° C., and the indicated temperature is no greater than ±2.5° C. while the ablation energy generator delivers a constant level of the ablation energy to the ablation electrode, wherein the irrigation pump flow control includes a proportional-integral-derivative controller (PID) algorithm configured to control the pumping rate based on the temperature difference.

2. The irrigated ablation system according to claim 1, wherein the medical probe comprises an intracardiac catheter.

3. The irrigated ablation system according to claim 1, wherein the irrigation fluid comprises a saline solution.

4. The irrigated ablation system according to claim 1, wherein the specified ablation temperature is at least 42° C.

5. The irrigated ablation system according to claim 1, wherein the temperature sensor comprises a thermocouple.

6. The irrigated ablation system according to claim 1, and comprising a temperature module configured to receive the temperature signal from the temperature sensor, to compute, based on the temperature signal, a temperature value, and wherein the processor is configured to control the pumping rate responsively to the temperature signal by controlling the pumping rate responsively to the temperature value.

7. The irrigated ablation system according to claim 1, wherein the ablation energy is selected from a list consisting of radio-frequency (RF) energy, high-intensity focused ultrasound (HIFU) energy and pulsed field ablation (PFA) energy.

8. The irrigated ablation system according to claim 1, wherein the at least one of the one or more fluid ports is configured to eject fluid along a longitudinal direction of the tube head on through the most distal surface of the ablation electrode configured to abut the myocardial tissue during ablation.

9. The irrigated ablation system according to claim 1, wherein the processor is configured to reduce the constant level of the ablation energy being applied based on the flow rate of the pump reaching a defined high flow rate and the temperature indicated exceeding a specified maximum temperature over a specified duration of time.

10. A method, comprising:
applying a specified level of ablation energy to an ablation electrode disposed at a distal end of a medical probe inserted into a chamber of a heart and in contact with a region of myocardial tissue;
receiving, by a processor from a temperature sensor disposed at the distal end, a signal indicative of a temperature of the region of myocardial tissue, wherein the signal is received tissue concurrently with conveying the ablation energy to the region of the myocardial tissue; and
dynamically controlling a pumping rate of irrigation fluid to one or more fluid ports extending through the ablation electrode responsively to the temperature signal so that a difference between a specified ablation temperature, which is no greater than 55° C., and the indicated temperature is no greater than ±2.5° C. while delivering a constant level of the ablation energy to the ablation electrode, wherein the dynamical controlling includes a proportional-integral-derivative controller (PID) algorithm configured to control the pumping rate based on the temperature difference, and wherein at least one of the one or more fluid ports extends through the most distal surface of the ablation electrode configured to abut the myocardial tissue during ablation.

11. The method according to claim 10, wherein the medical probe comprises an intracardiac catheter.

12. The method according to claim 10, wherein the irrigation fluid comprises a saline solution.

13. The method according to claim 10, wherein the specified ablation temperature is at least 42° C.

14. The method according to claim 10, wherein the temperature sensor comprises a thermocouple.

15. The method according to claim 10, and comprising receiving, by a temperature module, the temperature signal from the temperature sensor, computing, by the temperature module based on the temperature signal, a temperature value, and wherein controlling the pumping rate responsively to the temperature value comprises controlling the pumping rate responsively to the temperature value.

16. The method according to claim 10, wherein the ablation energy is selected from a list consisting of radio-frequency (RF) energy, high-intensity focused ultrasound (HIFU) energy and pulsed field ablation (PFA) energy.

17. The method according to claim 10, further comprising reducing the constant level of the ablation energy being applied based on the flow rate of the pump reaching a defined high flow rate and the temperature indicated exceeding a specified maximum temperature over a specified duration of time.

18. A computer software product, operated in conjunction with an intracardiac catheter having a distal end inserted into a chamber of a heart, a channel contained within the insertion tube and configured to deliver an irrigation fluid to the distal end, and one or more fluid ports coupled to the channel and disposed at the distal end, the product comprising a non-transitory computer-readable medium, in which program instructions are stored, which instructions, when read by a computer, cause the computer:
to apply a specified level of ablation energy to an ablation electrode disposed at the distal end and configured to convey ablation energy to a region of myocardial tissue with which the electrode is in contact;
to receive, from a temperature sensor disposed at the distal end, a temperature signal indicative of a temperature of the region of myocardial tissue; and
to control a pumping rate of irrigation fluid to the one or more fluid ports end responsively to the temperature signal so that a difference between a specified ablation temperature, which is no greater than 55° C., and the indicated temperature is no greater than ±2.5° C. while delivering a constant level of the ablation energy to the ablation electrode.

* * * * *